United States Patent [19]

Ohno et al.

[11] Patent Number: 4,641,036
[45] Date of Patent: Feb. 3, 1987

[54] METHOD OF AND APPARATUS FOR IMAGING SURFACE OF OBJECT AT HIGH TEMPERATURE

[75] Inventors: Jiro Ohno; Hirokatsu Yashiro, both of Kawasaki, Japan

[73] Assignee: Nippon Steel Corporation, Tokyo, Japan

[21] Appl. No.: 652,946

[22] Filed: Sep. 21, 1984

[30] Foreign Application Priority Data

Sep. 24, 1983 [JP] Japan .............................. 58-176748

[51] Int. Cl.$^4$ ............................................. G01N 21/00
[52] U.S. Cl. .................................... 250/574; 250/341; 250/554
[58] Field of Search ............... 250/554, 571, 573, 574, 250/341, 357.1; 356/336, 337, 338, 315

[56] References Cited

U.S. PATENT DOCUMENTS 4,129,780 12/1978 Laughlin ............................ 250/341
4,338,030 7/1982 Loos .................................... 250/574

Primary Examiner—Edward P. Westin
Attorney, Agent, or Firm—Pollock, Vande Sande & Priddy

[57] ABSTRACT

A method of imaging the surface of an object at high temperature includes the steps of: irradiating the surface of a high-temperature object with two different kinds of pulses of monochromatic light of a fundamental wave and a harmonic thereof; passing the reflected light from the surface of the object through both an interference filter which allows only the two different kinds of monochromatic light to pass and a high-speed optical switch thereby to remove any background light component; drawing out only the reflected light of the pulses and leading the same to an image generating mechanism where it is converted into an image; and controlling the voltage applied to the high-speed optical switch thereby to adjust the mixing ratio between two wavelengths. Also disclosed is an apparatus for imaging the surface of an object at high temperature which includes: a light pulse generator provided such as to be opposed to high-temperature object; and an interference filter, a half-mirror, a high-speed optical switch and an image generating mechanism which are successively disposed on the optical axis of the reflected light from the object.

5 Claims, 5 Drawing Figures

METHOD OF AND APPARATUS FOR IMAGING SURFACE OF OBJECT AT HIGH TEMPERATURE

BACKGROUND OF THE INVENTION

The present invention relates to a method of and apparatus for imaging the surface of an object at high temperature. More particularly, the invention pertains to a method of and apparatus for imaging the surface of an object at high temperature, most suitable for use in observing an object at high temperature in various industries or the surface condition of the object, for example, observation of the combustion state in a blast furnace or the state of molten iron and slag therein, the burning process of a combustion furnace burner, or the change of the surface condition of a steel ingot in a heating furnace or a steel ingot being hot-rolled.

When it is necessary to observe the high temperature object precisely, for example, microscopic particles such as soot in a fire flame or the surface condition of an object heated to high temperature, employment of spontaneous light radiated from the object permits only a red-hot image thereof to be obtained, and therefore, the obtained image only makes it possible to determine the profile of the object to be observed. If the ambient temperature is especially high and the entire surroundings are in an approximately red-hot state, it is difficult to determine even the profile of the object. In such a case, it is conventional practice to externally irradiate the surface of the object with an intense beam of light and to observe the surface of the object by the use of the reflected light from the surface. By this conventional method, however, it is not possible to obtain a precise observation, since there is a high level of background light noise caused by radiation.

SUMMARY OF THE INVENTION

Accordingly, a primary object of the invention is to provide a method of and apparatus for precisely observing microscopic particles such as soot in a fire flame or the surface condition of an object heated to high temperature, which is suitable for use in observation of the combustion state in a blast furnace or the state of molten iron and slag therein, the burning process of a combustion furnace burner, or the change of the surface condition of a steel ingot in a heating furnace or a steel ingot being hot-rolled.

To this end, according to the invention, there is provided a method of imaging the surface of an object at high temperature including the steps of: irradiating the surface of a high-temperature object with two different kinds of pulses of monochromatic light one pulse of which is a fundamental wave and the other pulse of which is a harmonic wave thereof; passing the reflected light from the surface of the object through both an interference filter, which allows only the two different kinds of monochromatic light to pass, and a high-speed optical switch, thereby removing any background light component; and passing only the reflected light of the pulses to an image generating mechanism where it is converted into an image. The method may further include the step of controlling the voltage applied to the high-speed optical switch thereby to adjust the ratio of intensities of the two wavelengths.

Further, according to the invention, there is provided an apparatus for imaging the surface of an object at high temperature including: a light pulse generator provided such as to direct light to a high-temperature object; and a half-mirror, an interference filter, a high-speed optical switch and an image generating mechanism which are successively disposed on the optical axis of the light reflected from the object.

The above and other objects, features and advantages of the invention will be clear from the following description of the preferred embodiment thereof, taken in conjunction with the accompanying drawings.

DESCRIPTION OF THE PREFERRED EMBODIMENT

Figure 1:
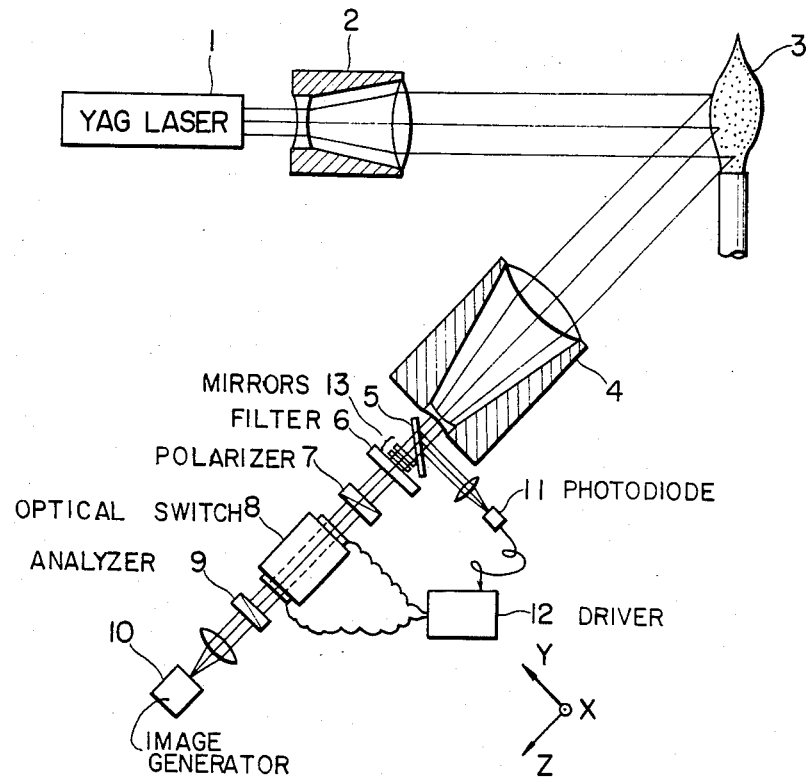
FIG. 1 is a schematic illustration of an apparatus for imaging the surface of an object at high temperature in accordance with the invention.

Referring first to FIG. 1, a light pulse generator, for example, a YAG laser 1, is provided with a higher-harmonic generator which generates not only a beam pulse of wavelength 1.06 $\mu$m as a fundamental wave but also a beam pulse of wavelength 0.53 $\mu$m as the second harmonic of the fundamental wave. Accordingly, a composite beam pulse is emitted in which the fundamental wave and the second harmonic have substantially comparable energy levels and are in the same direction. Reference numeral 2 denotes a beam expander 2 that expands the radius of the beam pulse. Reference numeral 3 represents a high-temperature object such as the flame of a burner. Reference numeral 4 denotes a condenser lens that condenses the beam reflected from the high-temperature object 3. Moreover, on the downstream side of the condenser lens 4 are disposed a half-mirror 5, a set of mirrors 13, an interference filter 6, a polarizer 7, a high-speed optical switch 8 constituted by a Pockels cell, an analyzer 9 and an image generating mechanism 10 such as an ITV camera. A photodiode 11 is employed to receive the light divided by the half-mirror 5. Further, a driver 12 is adapted to generate a voltage to be applied to the high-speed optical switch 8 in response to a signal from the photodiode 11.

According to the invention, a high-temperature object 3, for example, the flame of a burner, is observed by being imaged as follows. A YAG laser equipped with a harmonic generator is employed as the light pulse generator 1 and is allowed to generate two different kinds of pulses of monochromatic light having a wavelength of 1.06 $\mu$m and a wavelength of 0.53 $\mu$m. When the beam pulse is projected on the high-temperature object 3 through the beam expander 2, the beam is reflected from the high-temperature object 3. Since the high-temperature object 3 also radiates light spontaneously, the reflected light and the spontaneously radiated light superimposed thereon reach the condenser lens 4 where the composite light is condensed into a beam of light with a small radius. The beam is passed through the half-mirror 5 to reach the interference filter 6 which has the characteristics to allow only the light with the above-mentioned two wavelengths to pass, whereby the spontaneously radiated light which would be a background noise is removed and only the light constituted by the components with the two wavelengths pass. The resultant light is linearly polarized by the polarizer 7 and is then introduced into the high-speed optical switch 8. To the high-speed optical switch 8, on the other hand, is applied a high voltage generated by the driver 12 which is actuated by a signal from the photodiode 11 which delivers a signal when receiving the light obtained by dividing the beam pulse reflected from the half-mirror 5. As a result, the polarization of the beam pulse is changed so that the beam pulse passes through the analyzer 9 only during the high-voltage applied period. Accordingly, the beam pulse passing through the high-speed optical switch 8 at that time passes through the analyzer 9 and reaches the image generating mechanism 10, such as an ITV camera, where it is converted into an image. Thus, by observing the image, it is possible to visually check the surface condition of the high-temperature object 3.

Figure 2:
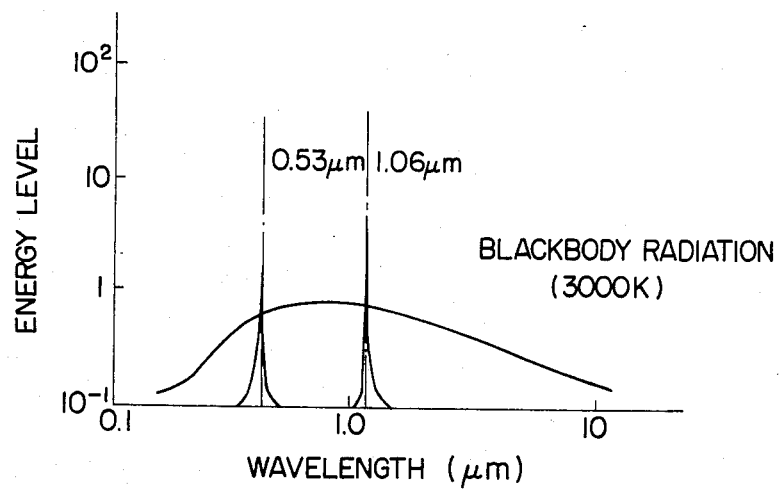
FIG. 2 is a graph showing the relationship between the wavelength and the energy level of the light reflected or radiated from the object, in the case of projecting a beam from a YAG laser on a high-temperature object and in the case of the blackbody radiation at the same temperature 3000° K.
Figure 3:
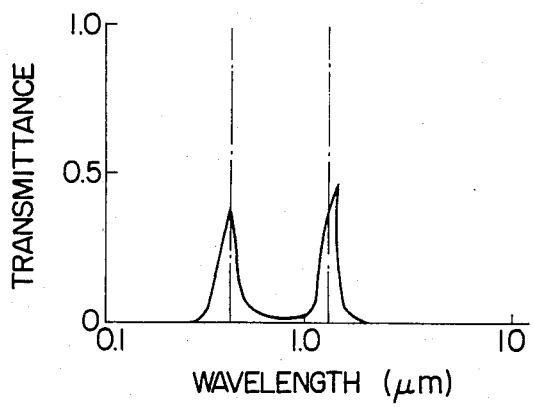
FIG. 3 is a graph showing the characteristics of a two-wavelength transmitting deposited-metal film interference filter employed in the invention.

The principle of the present invention will be explained hereinunder. In the case where the YAG laser is employed as the light pulse generator 1, as described above, the fundamental wave has a wavelength of 1.06 $\mu$m, while the second harmonic generated from the harmonic generator provided on the generator 1 has a wavelength of 0.53 $\mu$m, and this composite beam is projected on the high-temperature object 3. On the other hand, the spectrum of the radiation from a blackbody at 3,000° K. shows a relatively wide distribution (see FIG. 2). Accordingly, the light from the high-temperature object 3 is constituted by the reflected laser beam and the light spontaneously radiated from the high-temperature object 3, that is, the blackbody radiation, which are superimposed one upon the other. In this case, the blackbody radiation is evenly emitted also from the background of the object 3; therefore, it is necessary to remove the blackbody radiation in order to obtain a clear image of the object. For this reason, the superimposed beam from the high-temperature object 3 is led to a filter having transmission characteristics such as those shown in FIG. 3, thereby to remove the components of light other than those having wavelengths of 0.53 $\mu$m and 1.06 $\mu$m shown in FIG. 2, and the light at the time when the reflected laser beam is not present is removed by employing the high-speed optical switch 8 in the arrangement shown in FIG. 1. In this case, by properly designing the interference film of the interference filter 6, it is possible to form a two-wavelength transmitting filter which allows light of wavelength 0.53 $\mu$m and light of wavelength 1.06 $\mu$m to simultaneously pass therethrough. FIG. 3 shows characteristics of a two-wavelength transmitting deposited-metal film interference filter thus formed. Accordingly, when the reflected laser beam and the light spontaneously radiated from the high-temperature object 3 are passed through the interference filter 6, only the components having the two wavelengths are permitted to pass therethrough, thereby making it possible to greatly reduce the energy of the spontaneously radiated light which may result in a background noise.

The following is a description of the operation of the high-speed optical switch 8. As the light pulse generator 1, a YAG laser is employed which generates a giant beam pulse having a half-width of 10 ns and an output of 5 MW. The high-speed optical switch 8 is adapted to pass the light beam only when the beam pulse reaches the switch 8 but to be opaque during the other time so as to remove the background light at 1.06 $\mu$m and 0.53 $\mu$m. Therefore, it is necessary to apply a voltage from the driver 12 to the high-speed optical switch 8 in synchronism with the time when the beam pulse reaches the high-speed optical switch 8. On the other hand, light in a vacuum travels at a velocity of 3 m per 10 ns. Accordingly, any change of the position of the high-temperature object 3 varies the time required for the beam pulse to reach the high-speed optical switch 8. For this reason, it is necessary to change also the timing of generation of the voltage which is applied by the driver 12. Since the high-temperature object 3 can, however, freely change its position, there is a need for a switch operating method which is independent of any change of the position of the high-temperature object 3. In the invention, accordingly, a portion of the laser beam reflected from the high-temperature object 3 is taken out by the half-mirror 5, as described above, and is led into the photodiode 11 in order to actuate the photodiode 11 to generate a signal, which is transmitted to the driver 12, thus causing the driver 12 to generate a voltage which is applied to the high-speed optical switch 8. In this case, there is a delay of 25 ns±1 ns from the time when the photodiode 11 receives the light to the time when the voltage to be applied is generated. In consequence, the distance between the half-mirror 5 and the high-speed optical switch 8 is selected such as to be equal to the distance that light travels during the period of time which is equal to the above-mentioned delay, that is, 7.5 m. The distance between the half-mirror 5 and the high-speed optical switch 8 can be shortened by reducing the apparent distance in such a manner that the plane mirrors 13 are disposed between the half-mirror 5 and the interference filter 6 thereby to cause a multiple reflection, or a bundle of coiled image fibers are disposed therebetween.

Figure 4:
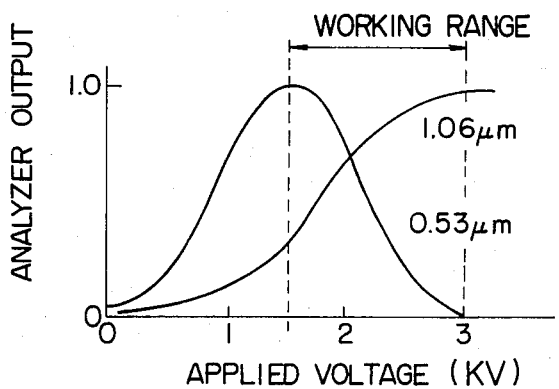
FIG. 4 is a graph showing the relationship between the voltage applied to a high-speed optical switch and the output of an analyzer employed in the invention.

The following is a description of an operation for changing the voltage which is applied to the high-speed optical swtich 8. A Pockels cell is employed as the optical switch 8, and in this case, it is possible to change the intensity ratio between the light components having the two wavelengths by making use of the properties of the Pockels cell that the plane of polarization of the transmitted light rotates by changing the voltage applied to the Pockels cell. FIG. 4 shows the relationship between the voltage applied to the high-speed optical switch 8 and the intensities of the light components having the two wavelengths which have passed through the analyzer 9 located following the high-speed optical switch 8. As will be clear from the drawings, changing the applied voltage between 1.5 kV and 3 kV causes a change in the ratio of intensities of the light components having the two wavelengths. More specifically, as the voltage is raised, the proportion of the light component of wavelength 1.06 $\mu$m increases, and the proportion of the light component of wavelength 0.53 $\mu$m decreases.

The ratio of intensities of the light components having the two wavelengths can be changed for the following reason: The polarizer 7 and the analyzer 9 are in orthogonal relation to each other with respect to the polarization of light. Therefore, if the direction of polarization by the polarizer 7 is assumed to be the direction X, the light passing through the polarizer 7 becomes a linearly polarized light with only the electric field $E_x$ and therefore is cut off by the analyzer 9 which passes only the electric field $E_y$. Accordingly, the energy does not reach the image generating mechanism 10. When an electric field is applied to the high-speed optical switch 8, however, the linearly polarized light having passed through the polarizer 7 becomes an elliptically polarized light, so that the component of the electric field vector ($E_y$) which passes through the analyzer 9 appears. Quantitatively, when $$P_x = |E_x|^2 = P_0 \cos^2 \frac{\Gamma}{2}, P_y = |E_y|^2 = P_0 \sin^2 \frac{\Gamma}{2},$$

where $$\Gamma = \frac{2\pi n_o^3 \gamma_{63}}{\lambda} V$$

represents retardation (optical phase difference) (where V is the voltage applied to the high-speed optical switch 8; $\gamma_{63}$, $n_o$ are constants of the crystal employed for the high-speed optical switch 8; and $\lambda$ is the wavelength of light). In other words, when the optical switch 8 is made "ON" or opened, only an amount of energy corresponding to $P_y = P_0 \sin^2 \Gamma/2$ is allowed to pass through analyzer 9. The amount of energy depends on $\lambda$ and V owing to the properties of $\Gamma$; therefore, when $\lambda$ is doubled, from 0.53 μm to 1.06 μm, V is required to be doubled also. This phenomena results in the properties in order to make $\Gamma$ at 1.06 μm equal to $\Gamma$ at 0.53 μm shown in FIG. 4.

Accordingly, changing the voltage applied to the high-speed optical switch 8 makes it possible to change the ratio between the light component of wavelength 1.06 μm and the light component of wavelength 0.53 μm as desired.

By thus changing the ratio, it is possible to clear the reflected image of the object to be measured. Although it is not generally possible to express the relationship between the ratio of intensities of the wavelengths and the definition of the image, changing the ratio is not only effective in obtaining a clear image but also makes it possible to emphasize the image of only a specific substance by independently obtaining images at two wavelengths and effecting synthesization of the two images thereby to obtain a pseudocolor image.

Figure 5:
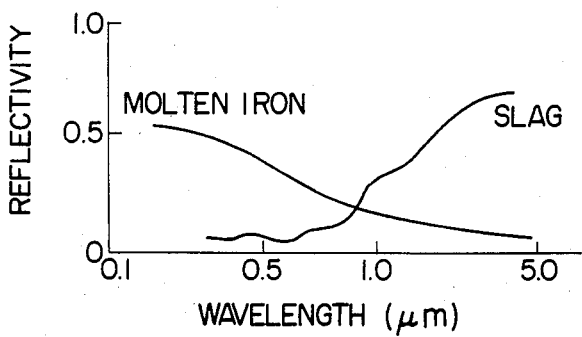
FIG. 5 is a graph showing the respective spectral reflectance curves of molten iron and slag.

Incidentally, each substance has different dependence of reflectivity on wavelength. FIG. 5 shows respective spectral reflectance curves of molten iron and slag. In the case of imaging an object in which substances are mixed together as in the case of molten iron and slag, it is only necessary to lower the applied voltage to 1.5 kV so that the proportion of the light component of wavelength 0.53 μm is increased when the image of molten iron is to be emphasized, and to raise the applied voltage to 3.0 kV so that the proportion of the light component of wavelength 1.06 μm is increased when the image of slag is to be emphasized.

Reflectivity of coke is little dependent on wavelength; hence, the image of coke is the clearest at an applied voltage of 2.5 kV at which both the light components are well reflected. More specifically, from the functional relation shown in FIG. 4, $f(X) = \alpha \sin^2 X + \sin^2 \frac{1}{2}X (\pi/2 < X < \pi)$, where $$X = \frac{\pi}{3,000(V)} V,$$

and the condition of the maximum value is given by $f'(X) = \alpha 2 \sin X \cos X + \sin \frac{1}{2}X \cos \frac{1}{2}X = 0$; hence, cos $X = -1/4\alpha$. The symbol $\alpha$ represents the ratio between the light component of wavelength 0.53 μm projected on the object and the light component of wavelength 1.06 μm projected on the object. If $\alpha$ is assumed to be 30%, then cos $X = -0.83$; hence, $X \approx 5/6\pi$. Consequently, the voltage is determined as follows: V=2.5 kV.

The following is a description of an example in which the present invention is employed in observation of the state of the inside of a blast furnace.

A YAG laser beam was projected on the blast furnace combustion zone through an optical waveguide tube incorporated in a water-cooled probe. The optical waveguide tube was constituted by a copper pipe having the inner surface thereof plated with silver so as to possess a high reflectivity. The light reflected from the blast furnace combustion zone was led to the outside of the furnace through the optical fiber incorporated in the water-cooled probe and was received by an image generating mechanism through a filter, a polarizer, an optical switch and an analyzer. As the result of thus observing the combustion zone, it was possible to obtain completely novel information through a clear image. In other words, although the prior art provides an image which has such a level of definition that only the profile of the red-hot lump coke can be seen, the image obtained by the present invention was completely different from the image conventionally obtained: When the voltage applied to the optical switch was set at 2.5 kV, the image of coke became clear, so that it was possible to observe the state of very fine coke dancing in the combustion zone, not to mention the state of the lump coke.

When the applied voltage was changed to 1.5 kV, the reflected light component of wavelength 0.53 μm was intensified. In the image obtained at that time, the molten iron was emphasized, and the luminance of the coke and the slag was small relative to that of the molten iron. It was found from the thus obtained image that the molten iron was distributed among pieces of coke.

At an applied voltage of 3.0 kV, the reflected light component of wavelength 1.06 μm was intensified, so that it was possible to obtain an image in which the slag was emphasized. From this image, it was possible to minutely observe the state wherein the slag was blown up above the combustion zone.

Thus, it was possible to obtain different kinds of image simply by changing the voltage applied to the optical switch, and it was possible to discriminate the coke, the molten iron and the slag one from another in a high-temperature condition and to observe the distributions thereof.

As has been described, the present invention makes it possible to obtain a precise stationary image of, for example, soot generated in the flame of a combustion furnace burner, or the image of the surface condition of a steel ingot in a heating furnace or the state of molten iron and slag or other various objects at high temperature. As a result, it is possible to minutely observe a fine profile, irregularities on the surface of an object, etc.

What is claimed is:

1. A method of imaging the surface of an object at a high temperature, comprising the steps of:
   irradiating the surface of a high-temperature object with pulses of monochromatic light of two different wavelengths, one of said wavelengths being a fundamental wavelength and the other of said wavelengths being a harmonic of said fundamental wavelength;
   passing light which is reflected from the surface of said object through both an interference filter which allows only said two different wavelengths of monochromatic light to pass and a high-speed optical switch, thereby to remove any background light component; and
   passing only the reflected light of the pulses to an image generating mechanism where it is converted into an image.

2. A method of imaging the surface of an object at high temperature, comprising the steps of:
   irradiating the surface of a high-temperature object with pulses of monochromatic light of two different wavelengths, one of said wavelengths being a fundamental wavelength and the other of said wavelengths being a harmonic of said fundamental wavelength;
   passing light which is reflected from the surface of said object through both an interference filter, which allows only said two different wavelengths of monochromatic light to pass, and a high-speed optical switch thereby to remove any background light component;
   passing only the reflected light of the pulses to an image generating mechanism where it is converted into an image; and
   controlling the voltage applied to said high-speed optical switch to thereby adjust the ratio of intensities of said two wavelengths.

3. A method of imaging the surface of an object at high temperature according to claim 2, wherein a trigger pulse for generating the voltage to be applied to said high-speed optical switch is obtained from a photodiode disposed preceding said switch, thereby to bring said high-speed optical switch into a transmitting state when the reflected light of the pulses reaches said high-speed optical switch independently of the position of said object.

4. An apparatus for imaging the surface of an object at high temperature, comprising:
   a light pulse generator provided such as to be opposed to high-temperature object; and
   a half-mirror for dividing light, an interference filter, a high-speed optical switch and an image generating mechanism which are successively disposed on the optical axis of light which is reflected from said object.

5. An apparatus according to claim 4, wherein a photodiode is provided on an optical axis of the light divided by said half-mirror and is connected to a mechanism for driving said high-speed optical switch.